United States Patent

Ehrlich

[11] 4,042,145
[45] Aug. 16, 1977

[54] SENSITIVITY DISC DISPENSER WITH TAMPER MECHANISM

[75] Inventor: Stephen Jeffrey Ehrlich, Randallstown, Md.

[73] Assignee: Becton, Dickinson and Company, East Rutherford, N.J.

[21] Appl. No.: 628,077

[22] Filed: Nov. 3, 1975

[51] Int. Cl.² ............................................... B65H 3/44
[52] U.S. Cl. ...................................... 221/94; 221/264; 221/234
[58] Field of Search .................... 221/93, 94, 264, 197, 221/233-235

[56] References Cited

U.S. PATENT DOCUMENTS

| 3,836,047 | 9/1974 | Darpentigny | 221/93 |
| 3,863,426 | 2/1975 | Courvalin | 221/93 X |

*Primary Examiner*—Allen N. Knowles
*Attorney, Agent, or Firm*—Kane, Dalsimer, Kane, Sullivan and Kurucz

[57] ABSTRACT

A sensitivity disc dispenser including a dispensing structure for housing a plurality of discs containing cartridges and including structure for simultaneously dispensing a disc from each cartridge through each one of a selected number of discharge ports containing a cartridge in a predetermined pattern. The discs are positioned from each cartridge into alignment with the respective discharge port and a tamping mechanism expels the disc through the respective discharge ports into a receiving dish. This tamping mechanism is used to eliminate the time-consuming manual tamping operation required in free fall disc dispensers. It also produces a very consistent spacing between discs. An adjustment device is provided to facilitate vertical positioning of a dispenser with respect to a receiving dish.

23 Claims, 11 Drawing Figures

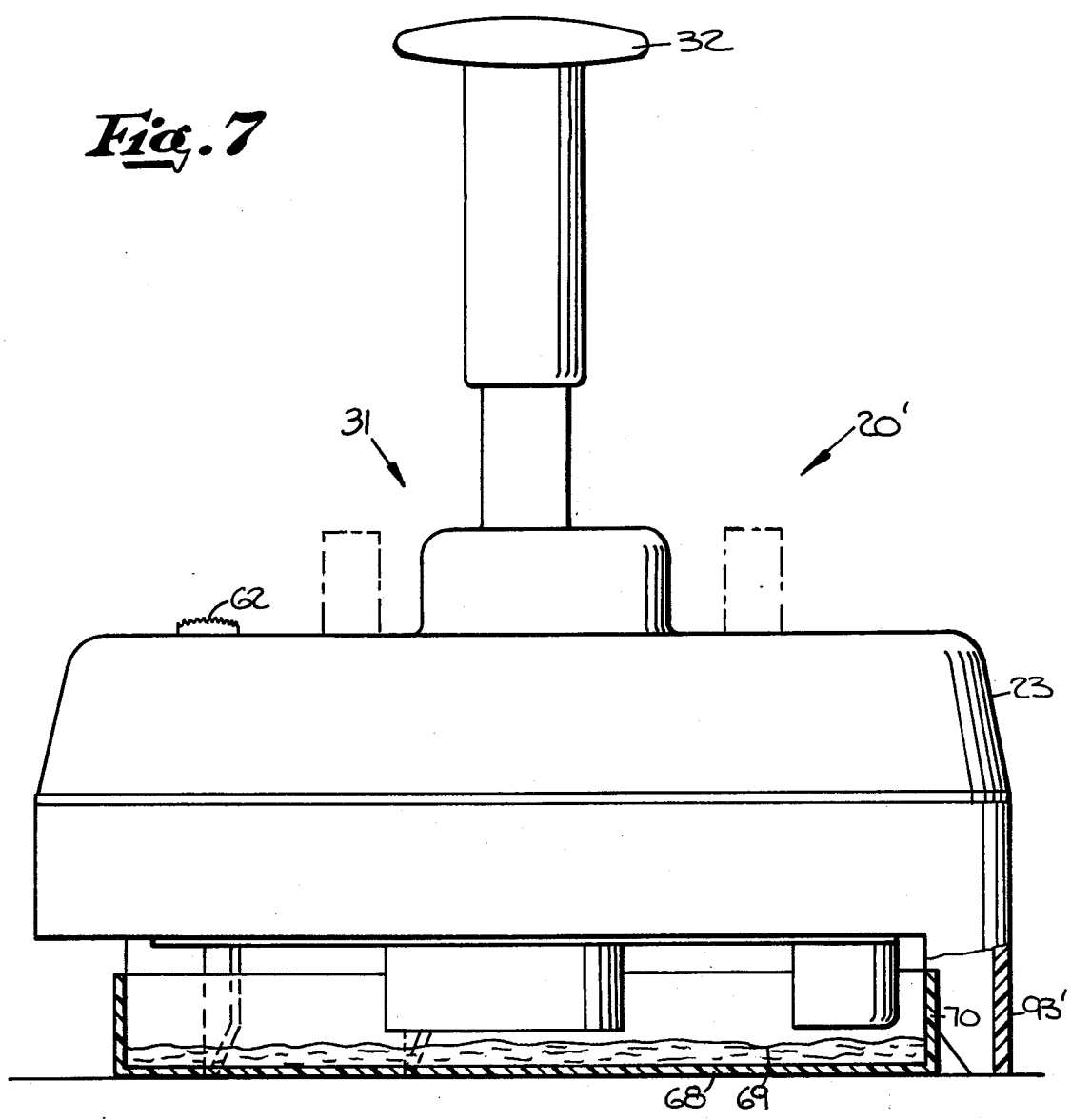
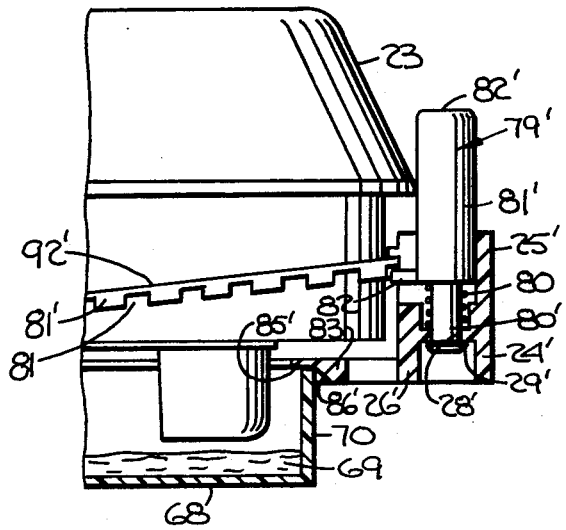
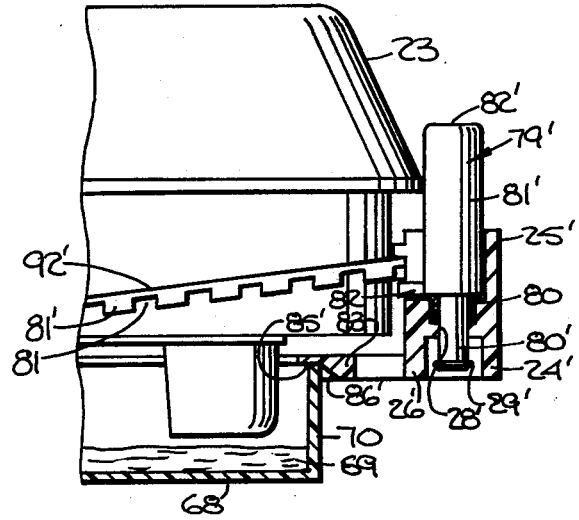

SENSITIVITY DISC DISPENSER WITH TAMPER MECHANISM

BACKGROUND OF THE INVENTION

There are many different types of disc dispensers available for dispensing sensitivity discs in a predetermined pattern onto the surface of a culture medium within a receiving dish. Certain types of structures are designed for dispensing a single disc at a time from a single cartridge and others dispense, for example, eight or 12 discs in a predetermined pattern. With the multi-disc dispensers there are separate disc containing cartridges for each position on the dispenser.

Certain types are rotational type of dispensing mechanisms where one portion of the dispenser rotates with respect to another in order to dispense the discs and others rely on a reciprocal vertical plunger type of arrangement which employs linkage to dispense a disc from each of the cartridges in the dispenser. In the majority of dispensers which have been used throughout the years, once the dispensers have moved a disc from a cartridge into alignment with a discharge port the disc is permitted to fall freely onto the culture medium. Whatever control is maintained over the disc in its free fall is determined by the diameter of the opening of the discharge port and the length of the surrounding port through which the disc freely falls. Another factor which determines control over the freely falling disc is the height of the bottom open end of the discharge port from the culture medium within the receiving dish.

Examples of dispensers which utilize the freely falling dispensing mechanism when dispensing a plurality of discs simultaneously in a predetermined pattern are disclosed in U.S. Pat. No. 3,394,846 to Carski et al and U.S. Pat. No. 3,300,087 to Kuypers. Various different approaches from the free fall method of dispensing have been attempted, the most significant of which for purposes of this invention is the system employed in the Darpentigny et al. U.S. Pat. No. 3,836,047.

The object in mind with all disc dispensers is to be able to provide a selected number of discs for a particular receiving dish and test to be accomplished therein in an accurate predetermined pattern. Of importance is reliability and versatility. It is important that the discs intended to be dispensed on a particular stroke be all dispensed in the most accurate and quick and efficient manner possible. The dispenser should be of the type which is reliable in the sense that repeated use for many times will result in the same accurate and complete dispensing of the desired number and pattern of discs. Naturally, cost is also significant and in this respect simplicity of structure is desirable as well as low cost in materials. It should also be kept in mind that the simpler the structure the greater the reliablity particularly when dealing with a low cost mass produced device. Furthermore, the more versatile and dependable the structure, the more desirable it is to the field. Different types of antibiotic tests require a different number and arrangement of discs and which in virtually all cases often depend upon accuracy in placement upon the culture medium.

SUMMARY OF THE INVENTION

With the above background in mind, it is among the primary objectives of the present invention to provide a sensitivity disc dispenser which is designed for accurately dispensing a pattern of discs simultaneously of any number from one to twelve in a predetermined pattern upon the culture medium in a receiving dish. The dispenser is designed so that upon one dispensing stroke the discs will first be placed into alignment with a dispensing port and then will be subjected to a tamping force to accurately and positively expel the required discs onto the culture medium at the desired position.

The structure employs a blocking means to restrain tamping mechanisms from passing through the discharge ports when particular cartridge locations on the dispenser are not being employed. In this manner, it is possible to dispense only a specific number of discs without the necessity of the tamping mechanism passing through the discharge port onto the culture medium at locations where no discs are being dispensed. If the tamping mechanism is allowed to touch the culture medium, cross contamination of the tamper and culture medium will occur.

This mechanical tamping means is used to eliminate the time-consuming manual tamping of discs required in free falling type disc dispensers. It also reduces the amount of time that the receiving dish must remain open and therefore reduces the chances of airborne contamination of the medium. The mechanical tamping means also provides a means of achieving a consistently precise disc location on the medium and eliminates manual repositioning of discs which are not located in the proper location if they have rolled away from the proper location or did not free fall properly.

The structure is designed so that insertion of a cartridge automatically activates the particular associated tamping mechanism so that only tamping mechanisms in alignment with discharge ports for inserted cartridges are in position to accomplish the tamping action.

It is another objective of the present invention to provide latch means so that the tamping action does not occur until the discs are appropriately dispensed into the discharge ports and are held therein at which time the latch means are released as part of the same dispensing stroke to permit the tamping mechanisms to drive the discs onto the culture surface.

Another objective is to provide an adjusting means on the dispensing structure to permit the relative height of the discharge ports with respect to the culture medium to be adjusted for facilitating the close control of dispensing the desired pattern of discs at the proper location on the culture medium.

A further object of the invention is to provide a lock mechanism to lock the desired number of cartridges in the appropriate cartridge receiving openings prior to the dispensing and tamping operations.

A still further object is to insure that the structure is of low cost design in manufacture and is easy and efficient to use as well as being dependable for multiple use over an extended period of time.

Still another object of the present invention is to provide an adjustment device which is adapted for use with a dispenser for permitting accurate vertical adjustment of the dispenser with respect to a receiving dish and to provide means for guiding the dispenser into proper alignment with the receiving dish for dispensing of discs.

In summary, the sensitivity disc dispenser of the present invention includes a dispensing structure for housing a plurality of discs containing cartridges and having means for simultaneously dispensing a disc from each cartridge through each one of a selected number of discharge ports containing a cartridge in a predetermined pattern. Means are provided for positioning a disc from each cartridge into alignment with the discharge port and tamping means are provided for expelling the discs through the respective discharge ports into a receiving dish so that a high consistent pattern of discs is produced and so that a timeconsuming manual operation is eliminated.

With the above objectives in mind, among others, reference is had to the attached drawings.

BRIEF DESCRIPTION OF THE DRAWINGS

FIG. 7 is a side elevation view of an alternative form of a dispenser of the invention;

FIG. 8 is a fragmentary sectional elevation view of the dispenser of FIGS. 1-6 showing the adjusting ring in position to prevent relative rotation of the dispenser with respect thereto;

FIG. 9 is a fragmentary sectional view thereof showing the pawl in position to permit rotation of the dispenser with respect to the adjusting ring;

DESCRIPTION OF THE PREFERRED EMBODIMENT

Figure 1:
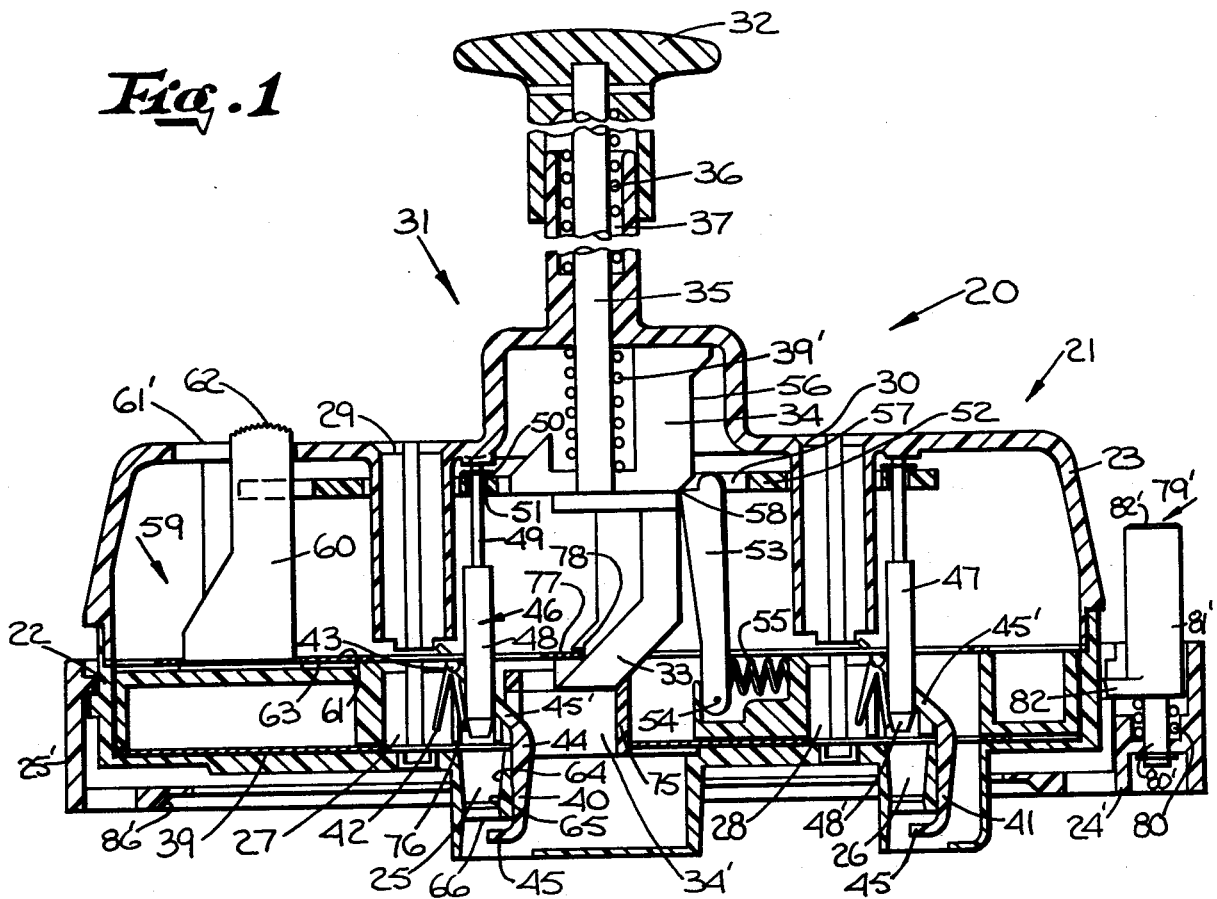
FIG. 1 is a sectional elevation view of the disc dispenser of the present invention and showing the dispenser in normal active positon without the presence of any dispensing cartridges.

FIG. 1 shows the dispenser 20 prior to its use and with all components in relaxed inactive position prior to insertion of cartridges for dispensing of discs. The dispenser includes a dispensing structure or housing 21 including a bottom half 22 and a top half 23. The bottom and top halves are shiftable vertically with respect to one another by the use of adjustable mechanism 24. This facilitates height positioning of the dispenser with respect to a receiving dish which will be discussed in further detail below. In the hollow interior of structure 21 are a plurality of spaced discharge ports such as ports 25 and 26. There may be any number of discharge ports, for example 12, and any number may be utilized depending upon the particular test and the number of discs to be dispensed.

Adjacent to each discharge port is a cartridge recess or opening such as opening 27 next to discharge port 25 and opening 28 next to discharge port 26. The cartridge openings extend through the dispensing structure and are open at the top as represented by openings 29 and 30 respectively through which can be extended a cartridge containing discs.

Centrally located in structure 21 is a dispensing plunger assembly 31 which extends out of the upper surface of top half 23 to terminate in a dispensing plunger handle or knob 32. The dispensing plunger structure terminates at the bottom end in an elbow-shaped cam rod or arm 33 which is mounted on a cam body 34. A slidable handle rod 35 interconnects with the plunger body 34 and extends through an appropriate opening in the top half 23 of structure 21 and has handle or knob 32 mounted on the upper extremity thereof. A spring 36 is housed in a surrounding recess 37 through which rod 35 extends and is under compression so as to engage with a surface of structure 21 at one end and an undersurface of knob 32 at the other end. Spring 36 tends to bias plunger rod assembly upward with respect to the remainder of dispensing structure 21. A full downward stroke achieved by pressuring knob 32 downward will move plunger rod assembly 31 downward with respect to the housing structure until elbow-shaped cam arm 33 is housed in cam receiving chamber 34'. Release of the knob 32 will permit spring 36 to return to its initial slightly compressed condition and shift the entire plunger rod assembly upward to its upper extremity which is determined by engagement between the upper surface of cam body 34 and the undersurface of top half 23.

Cam arm 33 extends through a slot in a sliding block 75 which is trapped in a dispensing plate 39 and the angular configuration of the elbow-shaped cam arm 33 will cause horizontal reciprocation of the dispensing plate upon reciprocal motion of plunger assembly 31 and sliding block 75. This type of action is described in detail in Carski et al U.S. Pat. No. 3,394,846. The dispensing plate 39 includes appropriate dispensing tabs for driving a disc from a cartridge within a cartridge recess and bringing it into alignment with the discharge port passageway adjacent thereto.

Each discharge port has associated with it a pivotal blocking arm such as arm 40 with respect to discharge port 25 and arm 41 with respect to discharge port 26. Each of these blocking arms includes a shorter activating lever or pin 42 which in the relaxed position extends downwardly and into the adjacent cartridge opening. At the end of the shorter arm 42 each blocking arm is affixed to the inner supporting structure by means of an appropriate pivot pin 43 and then extends in a longer elbow-like lever arm 44 which terminates in a blocking tab 45. In the normal relaxed positon as shown in FIG. 1, the shorter pin 42 extends into cartridge openings 27 or 28 respectively and the longer elbow-shaped arm terminating in the locking tab and pin is in engagement with the side wall of the discharge passage so that the blocking tab 45 prevents passage of any material or structure from the discharge port. An enlarged opening is in the elbow-shaped portion 44 for passage of a tamper mechanism or plunger such as plunger 46 with respect to discharge opening 25 or plunger 47 with respect to discharge opening 26. The openings 45' are large enough so that the tamping plunger rods can pass therethrough whether the blocking arms are in the blocking position as shown in FIG. 1 or when they are shifted to the open position as shown in further figures. The blocking arms such as 41 and 44 can be spring biased into the closed position as shown in FIG. 1 by a built in spring such as lever arm 76 on blocking arm 44 or it can be done by other additional spring means. If desired, no additional spring means may be employed and the part can be kept in the normal operating mode by gravity.

The tamper plunger rods such as rods 46 and 47 are provided for each discharge opening such as 25 and 26 respectively and include an enlarged body portion 48 at the lower end and a narrower shank portion 49 at the upper end. A locking ring or stop 50 is mounted on the end of the shank 49 distal from the body portion 48. Shank 49 is slidably mounted in opening 51 of a tamping plate 52. The opening 51 for each plunger rod shank 49 is smaller than the diameter of stop 50 and is smaller than the upper surface of body portion 48. Accordingly, movement of plate 52 with respect to plunger rods such as rods 46 and 47 is limited by the distance between the stop 50 and the upper rim of body 48 of each tamping plunger rod.

The tamping plate is normally retained in the upper position as shown in FIG. 1 by means of engagement with a latch arm 53 which is pivotally pinned at point 52 to an inner surface on supporting structure 21. A coil spring 55 biases latch arm 52 into the retaining position where it holds plate 52 and accordingly the tamper plunger rods in the upper inactive position. It also holds latch 53 into engagement with dispensing plunger body portion 34 so that it forms a cam follower to follow an appropriate exterior cam surface 56 along the vertical side of body portion 34 as the dispensing plunger rod assembly 31 is directed downward in a dispensing stroke. The upper surface of latch 53 engage with the undersurface of dispensing plate 52 to retain it in the upper inactive position prior to activation of the plunger. The arrangement of the components is such that as the dispensing plunger rod assembly 31 is directed downward, first a dispensing plate 39 is activated to position the appropriate discs into the discharge ports and then further movement of the dispensing rod assembly 31 in the downward direction shifts latch 53 into an appropriate opening 57 in the tamping plate so that the tamping plate can be forced downward onto a receiving surface of the supporting structure by the force of prebiased spring 39' and simultaneously the tamping rods can shift downward until they have expelled appropriate discs from the dispenser or are blocked from further downward movement by engagement with blocking tab 45 of a blocking arm. Alternatively, in the place of helical spring 39', other force mechanisms such as different types of springs can be utilized to direct dispensing plate 39 downward or, in the alternative, the plate can be permitted to fall freely under the force of gravity onto the receiving surface of the inner supporting structure. In the embodiment depicted, spring 39' is designed to be weaker than spring 36 so that when the plunger is released, spring 36 will overcome the force of spring 39' and return the assembly to the initial position as depicted in FIG. 1. Cam follower latch 53 contains a tapered follower point 58 which follows cam surface 56 and engages therewith through the force of biasing spring 55.

Also provided on the dispensing structure is a lock mechanism 59 which includes a locking bar 60 which extends upward through opening 61' in the dispensing structure 21 and terminates in a knurled upward surface 62 for finger engagement. The bar 60 is horizontally reciprocal within opening 61' and has its bottom rim 62 slidably channeled in recess 63 within the dispensing structure 21. Fitted on locking bar 60 is a locking plate 61 which is horizontally slidable along with the locking bar 60 in a reciprocal direction so as to shift into locking engagement with cartridges in the cartridge openings 27 and out of engagement with the cartridges when the cartridges are to be introduced or removed from cartridge openings 27. The locking mechanism 59 is quite similar to that shown in U.S. Pat. No. 3,394,846.

The discharge ports such as discharge port 25 and discharge port 26 have a tapered upper portion 64 which is wider at the top than at the bottom. The upper portion 64 terminates in a constricted intermediate portion 65 which communicates with a lower discharge portion 66 which again tapers outwardly in a downward position. This configuration for the discharge ports is designed to facilitate the dispensing operation as will be discussed in detail below.

In operation, the dispenser prior to use is in the position depicted in FIG. 1. The locking mechanism 59 has been horizontally withdrawn toward the right in the drawing to free the openings such as openings 27 and 28 to receive cartridges therein. The dispensing plunger assembly 31 is in the inactive upper position under the bias of spring 36 and accordingly the elbow-shaped cam arm 33 is in the upper position as well. The dispensing plate 39 has been shifted by arm 33 fully to the left thereby eliminating any interference with any portion of the cartridge openings. The tamping plate 52 and attached tamping plungers are in the upper position being retained in position by engagement with latch arm 53 which in turn is held in the latch position and against the body 34 of dispensing plunger assembly 31 by means of compression spring 55. In this position it should also be noted that the discharge ports such as 25 and 26 are open at the upper end and are blocked at the lower end by the blocking tabs 45.

Figure 2:
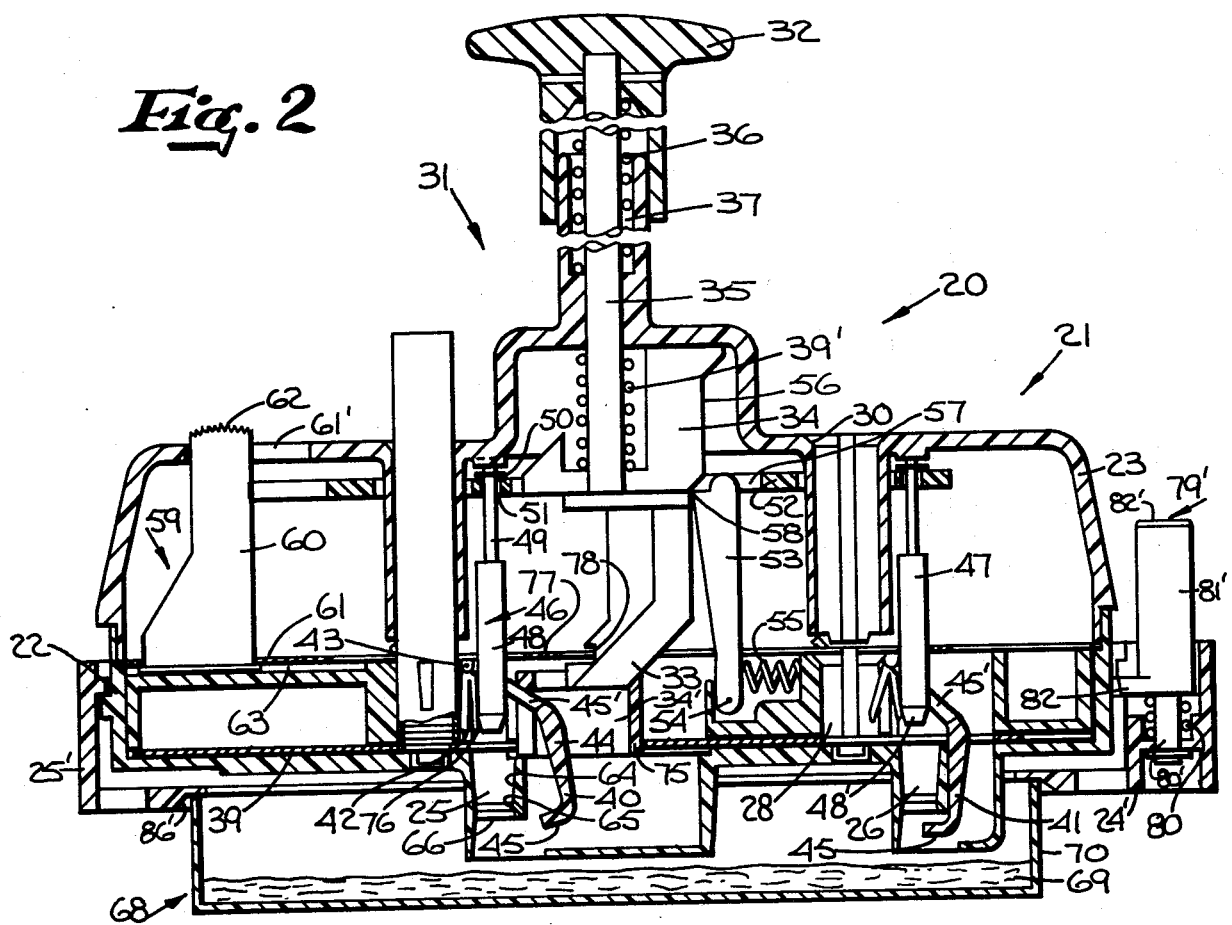
FIG. 2 is a sectional side elevation view thereof showing the dispenser in position with respect to a receiving dish and having a cartridge positioned for a dispensing operation.
Figure 3:
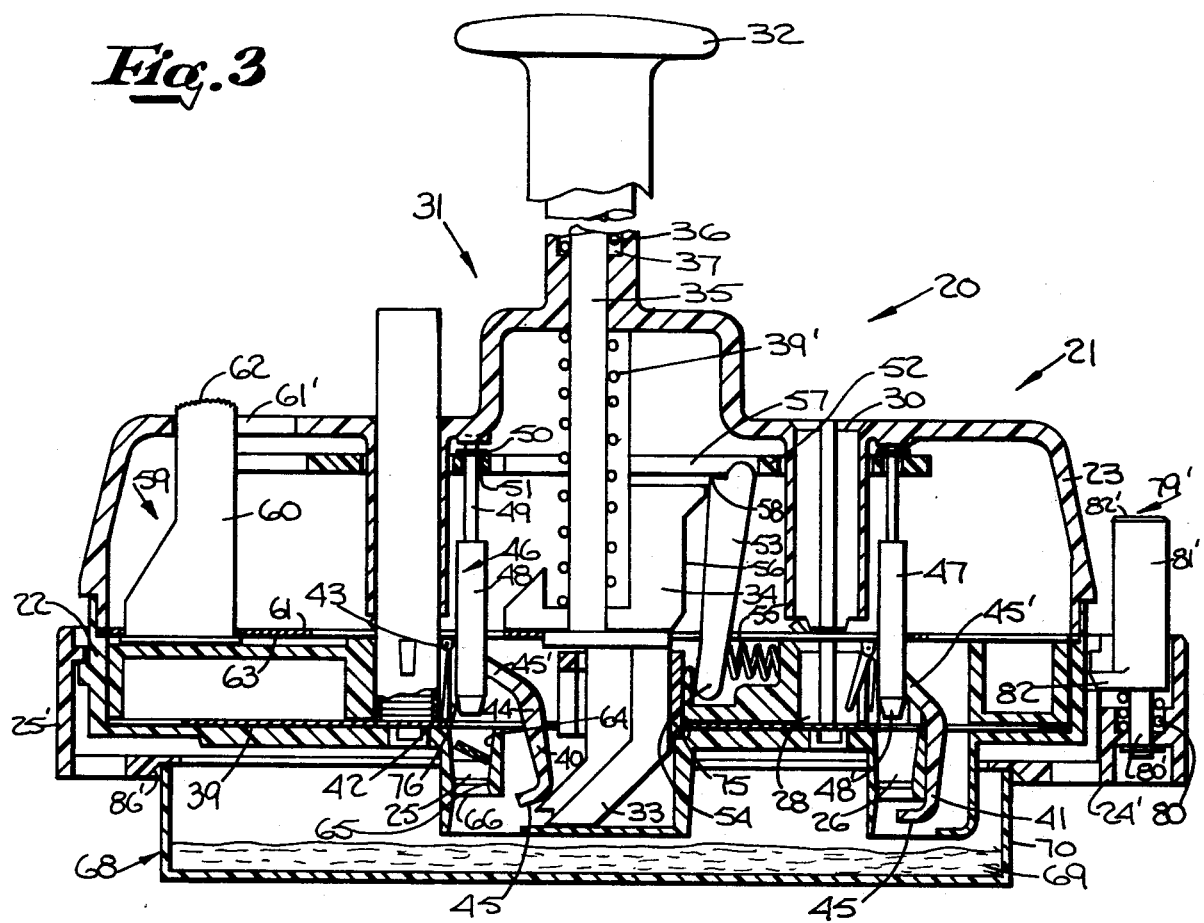
FIG. 3 is a sectional side elevation view thereof showing the dispenser of FIG. 2 with a disc having been dispensed into the discharge port passage and prior to the tamping operation.
Figure 4:
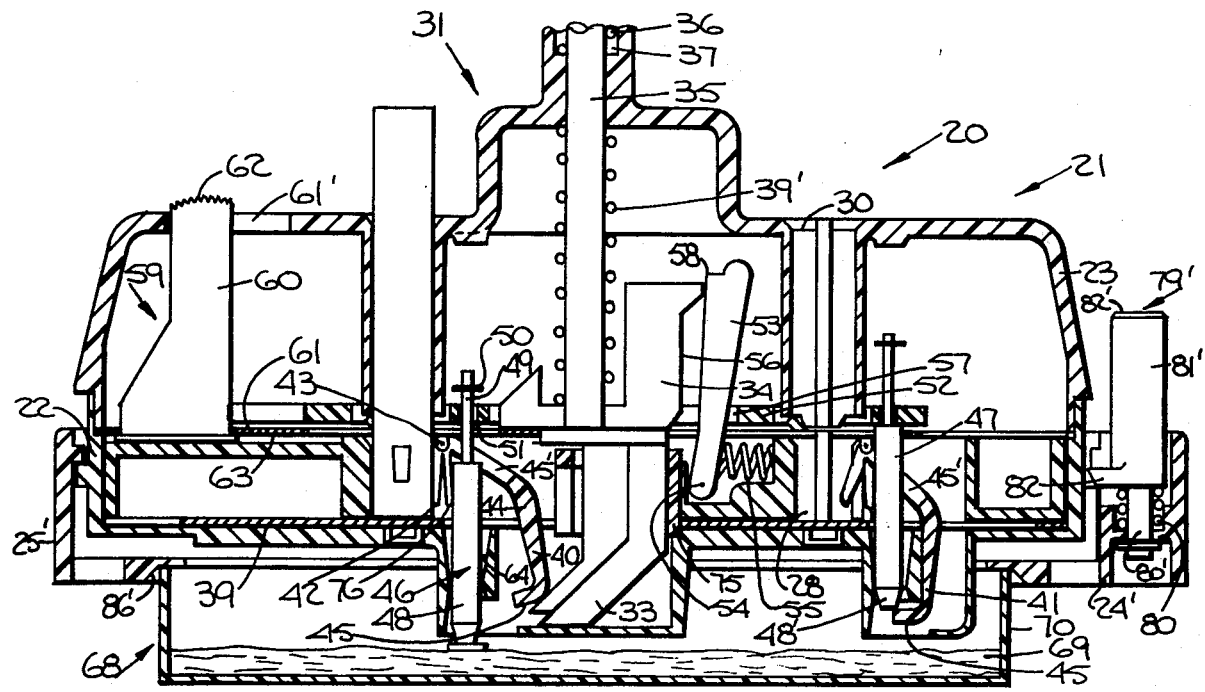
FIG. 4 is a sectional side elevation view thereof showing the position at the full downward movement of the dispenser at which time the tamping mechanism has tamped the disc from the discharge port onto the culture surface of the receiving dish.
Figure 5:
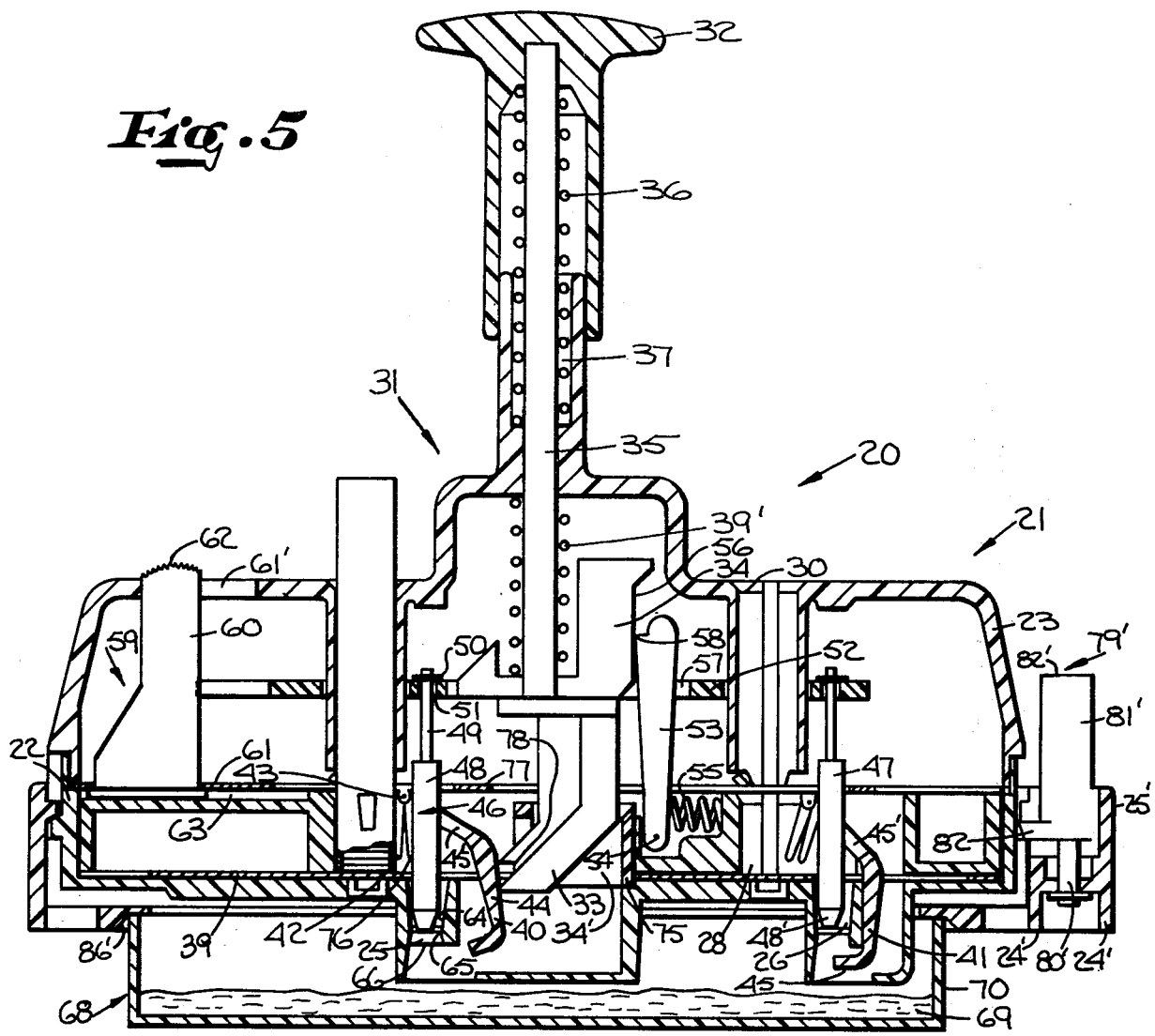
FIG. 5 is a sectional side elevation view thereof showing the position of partial return to the full upward relaxed position after a disc has been tamped onto the culture surface of the receiving dish.
Figure 6:
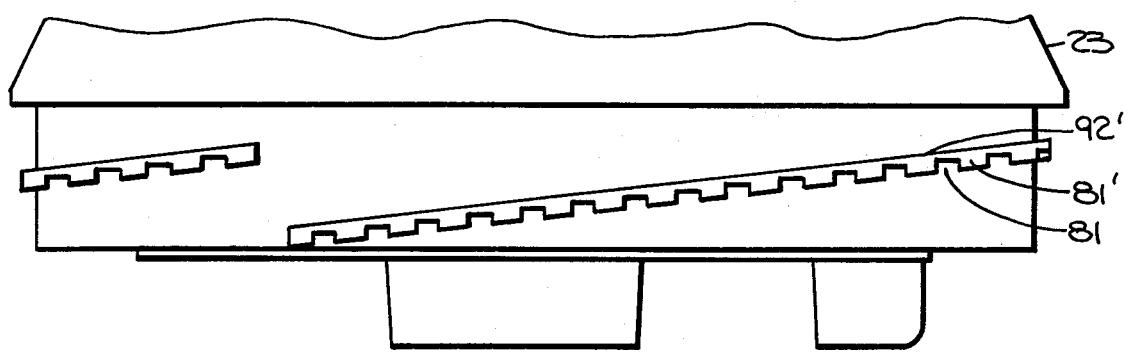
FIG. 6 is a fragmentary elevation view of the bottom end portion of the dispenser of the invention.
Figure 10:
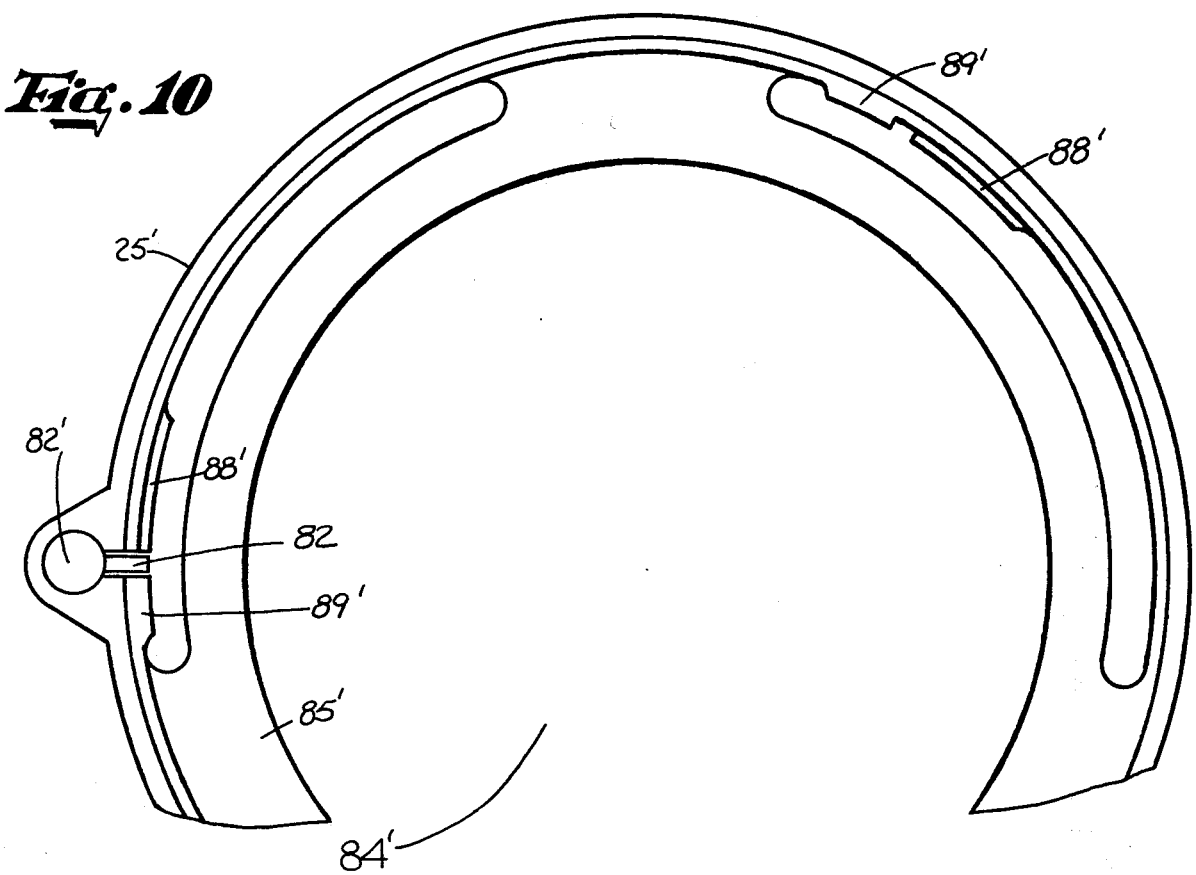
FIG. 10 is a top plan view of the adjusting ring.
Figure 11:
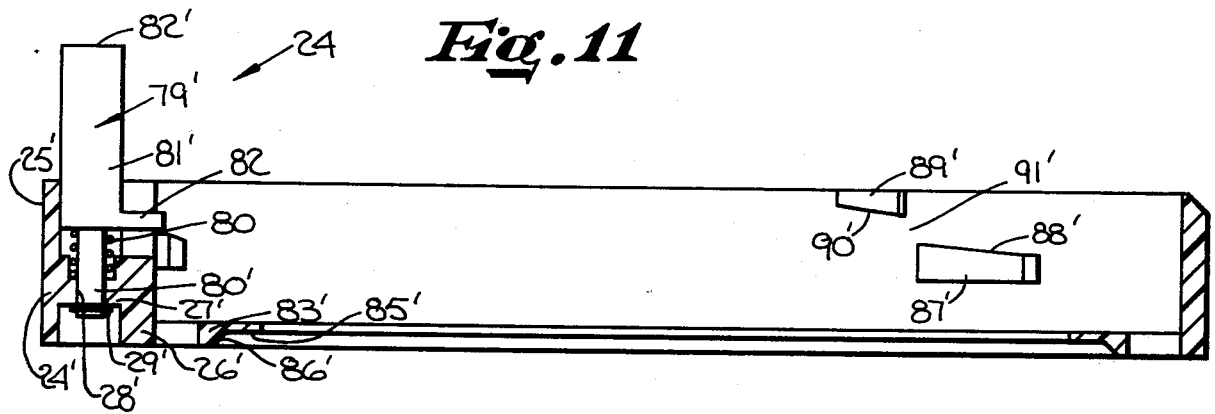
FIG. 11 is a sectional elevation view of the adjusting ring.

In use, the initial steps of operation are depicted in FIG. 2. The desired number of cartridges are inserted into the appropriate cartridge openings and as previously discussed the number of cartridges can be in any range depending upon the type of dispenser, such as on the order of one to twelve cartridge openings. For purposes of explanation, as depicted in FIGS. 2–4, one cartridge is depicted in position for the dispensing operation. The cartridge 67 has been inserted into cartridge opening 27 until it is fully seated at the bottom end thereof. In contrast, cartridge opening 28 has been left open and not in use. The cartridge is locked in position by shifting cartridge locking bar 62 to the left thereby engaging the body of cartridge 67 by locking plate 61 and retaining it in position. This shifting of plate 61 also unlocks the plunger rod assembly 31 by shifting section 77 of the locking plate 61 away from notch 78 in the rod assembly 31. Upon insertion of the cartridge 67 shorter arm 42 of blocking arm 40 has been pivoted down and away from opening 27 simultaneously pivoting the longer elbow-shaped arm 44 up and away from the discharge port 25 adjacent to cartridge opening 27. This action removes blocking tab 45 from the opening at the bottom end of discharge port 25. It should be kept in mind that since no cartridge has been inserted in opening 28, the bottom of discharge port 26 is still blocked by blocking tab 45. The bottom surface of dispensing structure 21 is then positioned on an appropriate receiving dish 68 with a culture medium 69 contained therein. The receiving dish has a bottom wall and a surrounding upwardly extending skirt 70, the upper edge of which receives the undersurface of dispensing structure 21.

Adjustment of the height of the discharge ports extending downwardly from the undersurface of dispensing structure 21 with respect to the receiving dish 68 is achieved through adjusting means 24 which regulates the relative position between the bottom of bottom half 22 and dish 68 and, accordingly, the relative position of the discharge ports with respect to dish 68. Adjustment means 24 includes an annular ring 24' having an outer upright side wall 25'. Spaced from the side wall 25' is an inner vertical wall 26' of lesser height than the outer wall and the two walls are interconnected by a lateral projecting wall 27' with a central aperture 28' therethrough. A button 79' is mounted on the ring 24' with a narrower dimensioned lower portion 80' extending through aperture 28' and slidably mounted therein. One end of narrower dimensioned portion 80' is restricted from complete upward passage through aperture 28' by means of a stop ring 29'. The other end of narrower dimensioned arm 80' is integrally formed with a wider upper portion of the button 81' which extends upward from ring 24' to form a finger engaging upper surface 82'. A helical spring 80 is captured between the undersurface of larger portion 81' and the upper surface of lateral wall 27' and tends to bias button 79' upward in the normal position. Engagement with upper surface 82' and depression of the button 79' will compress spring 80 and permit downward movement of the button with respect to the ring 24'. A lateral tooth or pawl 82 extends inwardly from button 79' in position for engagement with a ratchet surface formed on the bottom portion 22 of dispenser 20.

Spaced from inner wall 26' of ring 24' is a further annular ring 83' formed integrally with ring 24' and including a central aperture 84' and an inner receiving lip 85' to engage with the upper rim of side wall 70 of receiving dish 68. The dish is captured in position by beveled outer surface portion 86 of ring 83' so that relative positioning of the dish with respect to the ring and accordingly the dispenser is automatically achieved.

The inner surface of outer ring 24' contains a plurality of pairs of cams, for example three or four spaced pairs, with the lower cam 87' having an inclined upper surface 88' and the upper cam 89' of the pair having an inclined lower surface including in the same direction so as to form an upwardly extending pathway 91' therebetween.

Pathway 91' between each pair of spaced cams on the adjusting ring is designed to receive helical cam surface 92' on the outer surface of lower half 22 of the dispenser. The helical cam surface 92' includes the plurality of spaced ratchet teeth 81' and appropriate notches 81 therebetween. In this manner, adjusting ring 24' can be interengaged with dispenser 20 by threading helical cam surface 92' through pathways 91' on the inner surface of ring 24'.

When button 79 is in the normal relaxed position, pawl 82 is positioned in a notch 81 so as to prevent relative rotation of the ring with respect to the dispenser and accordingly to prevent vertical shifting of the ring with respect to the dispenser and accordingly to prevent vertical shifting of the discharge ports. Upon depression of button 79', pawl 82 is moved downward out of engagement with notch 81 so as to permit relative rotation between the ring and the dispenser and consequent vertical adjustment of the dispenser when the ring is positioned with surface 85' located on the upper rim of side walls 70 of a receiving dish 68. When sufficient adjustment has occurred so as to locate the discharge port at the desired height with respect to the culture surface 69 within the receiving dish, button 79' can be released whereupon spring 80 will return the button to the initial position with pawl 82 once again in engagement with an aligned notch 81 so as to lock the dispenser in fixed vertical position. In this manner, the height of the dispenser can be adjusted at will and in very accurate increments.

Alternatively, where very delicate height adjustment is not necessary, it is possible to merely provide the dispenser 20', as shown in FIG. 7, with an outer depending skirt 93' in place of the adjusting ring with the skirt designed to rest on the surface containing the receiving dish 68. In place of skirt 93', legs can be employed for the same purpose with the ultimate result being a permanent vertical positioning of the discharge ports with respect to the supporting surface and with respect to the culture medium 69 contained within a receiving dish 68. Appropriate resting surfaces can be provided on the undersurface of the dispenser to engage with the upper rim of side wall 70 of the dish and the dispensing action can be accomplished in the same manner as with respect to the embodiment discussed above. The only difference in operation is that there is no fine vertical adjustment provided for the discharge ports. In many environments and in many uses, this is adequate for the purpose to which the dispenser is being employed.

Returning to the next step in the dispensing operation sequence reference is made to FIG. 3 where the dispensing plunger assembly 31 has been depressed partially downward so that cam arm 33 displaces dispensing plate 39 horizontally to displace a disc from the bottom of cartridge 67 so that it falls into the enlarged upper portion 64 of dispensing port 25. The disc will fall freely until it is stopped in position by constricted portion 65. Tamping plate 52 and accordingly tamping plungers 46 and 47 have not yet been released and the tamping action has not occurred. Continued downward depression of knob 32 and accordingly dispensing plunger assembly 31 will bring the assembly into the position as depicted in FIG. 4. The body portion 34 of dispensing plunger assembly 31 will have extended downwardly far enough to have its cam surface displace latch arm 53 until it is aligned with the opening 57 in the tamping plate 52. This permits the tamping plate to be directed downward by spring 39' until it bottoms against a receiving surface on the interior of supporting structure 21 as depicted in FIG. 4. In turn, this permits the tamping plungers 46 and 47 to fall freely until stopped. In the case of plunger 46 with the blocking arm 40 having been moved out of the blocking position, the plunger will extend downward through opening 45 in the blocking arm and through discharge port 25 and engage with the disc 72 held by constriction 65 therein and continue to move downward and force the disc 72 onto the culture surface 69 tamping the disc in position at the precise disc spacing location on the culture surface which eliminates the time required to manually reposition discs which may be too close together. The downward movement of plunger 46 will be restrained by the disc contact with the surface of the medium. If the device is activated over either nothing or an empty plate, the plunger would be restrained by reengagement of stop 50 at the upper end of shank portion 49 and the upper surface of dispensing plate 52 now in the lower position. This mechanical tamping mechanism is used to eliminate the time consuming manual tamping operation required in free fall type disc dispensers. It also reduces the time required to keep the receiving plate open and therefore reduces the chances of airborne contamination of the medium. In contrast, with respect to tamping rod 47, it is stopped from full downward movement by engagement of its bottom edge with blocking tab 45. In this manner, the tamping mechanism associated with a cartridge opening not in use will be restrained from engaging with and affecting the surface of the culture medium 69. By permitting the tamping plungers to drive appropriately positioned discs into exact position on the culture surface, the danger of failure of the discs from being fully dispensed from the dispenser on the dispensing stroke is eliminated and additionally the disc is guided by the tamping plunger to the precise location on the culture medium. Accordingly, reliability and preciseness of disc placement and test reliability is achieved.

It should be kept in mind that the entire dispensing operation including the tamping operation is achieved upon one downward stroke of the dispensing plunger assembly 31. When knob 32 is released the dispensing plunger will return upward to the relaxed position under the bias of spring 36 and will return the tamping plate and tamping plungers to the upper positions as depicted in FIG. 1 as well as permitting latch 53 to be returned by spring 55 to its latching position to hold the tamping arrangement in the upper position of FIG. 1. The dispensing structure is then ready for repeated use.

The structure of the present invention is designed for manufacture of metal or plastic, employs a minimum number of parts and can be quickly and efficiently assembled and operated.

The present dispensing structure is designed to alleviate the danger of contamination of the structure from contact with culture medium so that it can be used repeatedly and so that the operator is not endangered from coming into contact with contaminating materials. To facilitate this condition, the design of structure is such that only the forward tip portions of the tamping plungers ever come into close contact with the culture medium. Furthermore, should they touch a contaminating surface, the tips are beveled so that as they are withdrawn back into the dispensing structure they will not come into contact with any other portions of the structure. Additionally, only the plungers which drive a disc onto the surface extend out of the dispensing structure and into close relationship to the culture medium 69. The remaining plungers are held within the dispenser by retaining tabs 45. Consequently, there is no danger of the plungers coming into direct contact with the culture surface at locations where no discs are being dispensed. It should also be kept in mind that since the tamping plungers are withdrawn back into the dispenser after the dispensing stroke has been accomplished, there is little danger of contamination of the operator when transporting or handling the dispenser for a further use.

Thus the several aforenoted objects and advantages are most effectively attained. Although several somewhat preferred embodiments have been disclosed and described in detail herein, it should be understood that this amendment is in no sense limited thereby and its scope is to be determined by that of the appended claims.

What is claimed is:

1. A sensitivity disc dispenser comprising; a dispensing structure for housing a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the discs through the respective discharge ports into a receiving dish and means for permitting dispensing through a selected number of ports less than the total number of ports.

2. A sensitivity disc dispenser comprising; a dispensing structure for housing a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the discs through the respective discharge ports into a receiving dish, the tamping means includes a plurality of tamping plungers reciprocally mounted within the dispensing structure with each tamping plunger in alignment with a discharge port, a tamping plate reciprocally mounted in the housing and having means thereon to mount the plurality of tamping plungers, each tamping plunger having a main body portion of larger diameter and a stem portion of smaller diameter extending upwardly therefrom, a stop means on the end of the stem distal from the body portion, apertures in the tamping plate with each tamping plunger having its stem slidably mounted in the aperture with the distance of travel of the tamping plunger being determined by the distance between the stop means on the distal end of the stem and the adjacent end of the body portion, the plate being shiftable between an upper inactive condition in which the tamper plungers are each respectively positioned in an aperture in the tamping plate with the stop means on the stem in engagement with the upper surface of the tamping plate and an active condition when the tamping plate is permitted to fall and shift to its lower position whereupon the tamping plungers will correspondingly be permitted to fall downwardly until the body portion extends through the discharge port unless arrested by engagement between some portion of the tamping plunger and an arresting surface.

3. The invention in accordance with claim 2 wherein a latch mechanism is provided for release of the tamping plate and tamping plungers when desired.

4. The invention in accordance with claim 3 wherein the latch mechanism includes a pivotally mounted arm within the dispensing structure, a spring means biasing the arm into engagement with surfaces of the tamping plate so as to hold the tamping plate normally in the upward inactive position, the arm adapted to be pivoted out of engagement with the surfaces of the tamping plate so as to permit the tamping plate to fall until it engages with appropriate surfaces in the housing to arrest its downward movement.

5. The invention in accordance with claim 1 wherein shiftable blocking means is provided in the dispensing structure and is shiftable between a position at which it blocks the exit aperture of the discharge port and a position at which it opens the discharge port.

6. A sensitivity disc dispenser comprising; a dispensing structure for housing a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the discs through the respective discharge ports into a receiving dish, shiftable blocking means being provided in the dispensing structure and being shiftable between a position at which it blocks the exit aperture of the discharge ports and a position at which it opens the discharge port, the blocking means includes a pivotally mounted arm having one shorter leg normally extending into an opening for receiving a cartridge and having a longer irregularly elbow-shaped leg terminating in a blocking tab normally extending at least partially across the opening of the discharge port to thereby prevent discs and tamping plungers from passing therethrough, the blocking means being pivotally mounted so that when a cartridge is inserted into a recess in the dispensing structure adjacent to a discharge port, the shorter leg will be pivoted away from the opening thereby pivoting the longer elbow-shaped leg and blocking tab away from the exit of the adjacent discharge port so as to permit a disc and tamping plunger to pass therethrough.

7. The invention in accordance with claim 6 wherein the blocking means are spring biased into the blocking position by spring biasing means.

8. The invention in accordance with claim 1 wherein the dispensing structure includes a housing, the means for positioning a disc from each cartridge mounted in a cartridge opening in the dispensing structure into an alignment with a discharge port includes a reciprocally movable horizontal dispensing plate with a tab and recess for each discharge port and adjacent cartridge opening, a dispensing plunger assembly on the housing and extending into the housing and terminating in a cam surface in engagement with the dispensing plate so that reciprocal movement of the plunger assembly will cause simultaneous reciprocal movement of the dispensing plate and dispense a disc from each cartridge contained in the structure into alignment with a discharge port.

9. The invention in accordance with claim 1 wherein seating means is on the dispensing structure to facilitate seating of the structure over a receiving dish with the discharge ports in alignment with the interior of the dish.

10. The invention in accordance with claim 9 wherein adjusting means is on the supporting structure to facilitate adjustment of the height of the discharge ports with respect to the interior of the receiving dish when the dispensing structure is mounted on a receiving dish.

11. A sensitivity disc dispenser comprising; a dispensing structure for housing a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the discs through the respective discharge ports into a receiving dish, seating means on the dispensing structure to facilitate seating of the structure over a receiving dish with the discharge ports in alignment with the interior of the dish, adjusting means on the supporting structure to facilitate adjustment of the height of the discharge ports with respect to the interior of the receiving dish when the dispensing structure is mounted on a receiving dish, the adjusting means includes a circular ring having cam surfaces on the interior thereof and a shiftable button including a pawl extending therefrom inwardly from the ring surface, a spring biasing the button toward the upper rim of the ring, the lower end of the housing having a spiral cam surface including a plurality of spaced ratchet teeth thereon, the cam surface is on the interior of the adjusting ring adapted for interengagement with the spiral cam surface on the lower end of the housing so that relative rotation therebetween causes axial movement between the ring and the housing, the button being normally biased so that the pawl is in engagement with a ratchet tooth on the housing to prevent relative rotation between the ring and the housing and when the button is shifted to bias the spring the pawl is removed from interengagement with the ratchet tooth permitting relative rotation between the ring and the housing and consequent vertican adjustment therebetween, and seating means on the ring for mounting the ring on the rim of a receiving dish so that when it is coupled with the housing the discharge ports of the housing will be aligned with the interior of the receiving dish.

12. The invention in accordance with claim 1 wherein a lock mechanism is positioned in said dispensing structure and extending through said dispensing structure, the lock mechanism adapted to be shiftable between a first position at which it locks each cartridge in position in the dispensing structure and a second position at which it will permit the cartridges to be inserted or removed from the dispensing structure and can simultaneously prevent the operation of the plunger assembly.

13. The invention in accordance with claim 8 wherein a biasing means is provided to bias the plunger rod upwardly with respect to the dispensing structure to thereby return the plunger rod, dispensing plate, and tamping mechanism to the inactive positions when released after the dispensing stroke is complete.

14. A sensitivity disc dispenser comprising; a dispensing structure for housing a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the discs through the respective discharge ports into a receiving dish, each discharge port has a wider open top end tapering to an intermediate constricted point and then tapering openly again to the bottom end, the intermediate constricted portion being of slightly lesser diameter than a disc being dispensed so as to form an interference fit with the disc and retain the disc in fixed position at that point until the tamper plunger forces the disc past the constricted point and out of the discharge port onto the receiving surface of the dish.

15. The invention in accordance with claim 1 wherein there are twelve spaced cartridge openings in the dispensing structure.

16. The invention in accordance with claim 8 wherein the plunger rod is interconnected with the tamping means so that downward movement of the plunger rod first dispenses a disc from each cartridge into alignment with a corresponding discharge port and then continued downward movement of the plunger activates the tamping means to complete expulsion of the discs through the respective discharge ports into a receiving dish.

17. The invention in accordance with claim 16 wherein biasing means is provided to bias the plunger rod upwardly with respect to the dispensing structure to thereby return the plunger rod, dispensing plate, and tamping mechanism to the inactive position when released after the dispensing stroke is complete, and second biasing means to urge the tamping means downward after activation thereof with the plunger rod biasing means being greater than the tamper biasing means thereby facilitating return of the plunger rod, dispensing plate and tamping mechanism to the inactive positions.

18. An adjustment device adapted to be coupled with a sensitivity disc dispenser adapted to dispense a plurality of discs through a plurality of corresponding discharge ports in a predetermined pattern into a receiving dish comprising:

a ring having an annular side wall and supporting structure for a reciprocally movable button having a laterally inwardly extending pawl adapted for interengagement with receiving surfaces disposed on the dispenser, cam surfaces on the inner wall of the adjusting ring adapted to interengage with a pathway on the exterior surface of the dispenser so that relative rotation between the dispenser and adjustment ring will cause vertical reciprocation therebetween, the pawl positioned so as to interengage with a receiving surface when the ring is assembled with a dispenser and to be disengaged from the receiving surface when the button is shifted, the ring having means thereon for mounting the ring to a receiving dish and positioned so that when the ring is coupled with a dispenser and located on the receiving dish the discharge ports of the dispenser will be aligned promptly with the receiving dish.

19. The invention in accordance with claim 18 wherein button biasing means is provided to normally urge the pawl into engagement with a receiving ratchet surface when the adjusting ring is coupled with a dispenser.

20. The invention in accordance with claim 19 wherein a button supporting structure is provided and is formed by an inner shorter wall portion spaced from a portion of the wall of the ring and having a lateral supporting surface extending therebetween with an aperture therethrough, the button including a narrow diameter portion extending through the aperture and reciprocally movable with respect thereto, stop means on the lower end of the narrow diameter portion of the button to restrict the upward movement thereof, the upper portion of the button being of larger diameter than the portion extending through the aperture and extending above the side wall of the ring to provide a finger engaging surface, the larger portion of the button being larger than the aperture through the lateral wall to restrict downward movement of the button, a helical spring captured between the undersurface of the larger portion and the surface of the lateral wall surrounding the aperture and the spring being in surrounding engagement with the narrower diameter portion of the button so that the spring normally biases the button upward until the stop means restricts the upward movement thereof and the spring permits downward movement of the button when pressure is applied to the upper surface thereof, the pawl extending laterally inward from the larger diameter portion of the button in position for interengagement with the ratchet teeth on a dispenser when coupled thereto.

21. The invention in accordance with claim 18 wherein the cam surfaces on the inner surface of the wall of the ring include at least one pair of inwardly extending projections adjacent to one another and vertically spaced apart, the upper surface of the lower projection and the lower surface of the upper projection being inclined upwardly in the same direction so that when the projections are coupled with a helical surface on a dispenser relative rotation between the ring and the dispenser will cause corresponding relative movement between the ring and the dispenser.

22. The invention in accordance with claim 18 wherein the mounting means for positioning the adjusting ring on a receiving dish includes an annular rib inwardly spaced from the wall of the ring and having an inner edge for engagement with the lower end of the dispenser to guide the dispenser in the proper location with respect to the receiving dish and having an outer portion with a beveled inner surface to form a shoulder and restrict lateral movement of the receiving dish with respect to the adjusting ring when mounted thereto.

23. The invention in accordance with claim 18 wherein the pawl on the button is adapted for engagement with a helical ring on a dispenser containing a plurality of spaced notches in the undersurface so as to form ratchet teeth whereby engagement between the pawl and a notch will restrict the rotational movement between the adjusting ring and the dispenser and displacement of the pawl from a notch will permit rotational movement of the dispenser with respect to the ring.

* * * * *